(12) United States Patent
Bettencourt

(10) Patent No.: US 11,103,326 B2
(45) Date of Patent: Aug. 31, 2021

(54) WARMING OVEN

(71) Applicant: HUESTIS MACHINE CORPORATION, Bristol, RI (US)

(72) Inventor: Stephen Bettencourt, Warren, RI (US)

(73) Assignee: HUESTIS MACHINE CORPORATION, Bristol, RI (US)

(*) Notice: Subject to any disclaimer, the term of this patent is extended or adjusted under 35 U.S.C. 154(b) by 23 days.

(21) Appl. No.: 14/796,554

(22) Filed: Jul. 10, 2015

(65) Prior Publication Data

US 2017/0010004 A1 Jan. 12, 2017

(51) Int. Cl.
*A61B 90/18* (2016.01)

(52) U.S. Cl.
CPC .................. *A61B 90/18* (2016.02)

(58) Field of Classification Search
CPC ...... F24C 15/16; F24C 15/166; F24C 15/325; F24C 7/085; F24C 7/088
USPC ....... 219/391, 392, 400, 385, 405, 407, 417; 604/291; 99/473, 474
See application file for complete search history.

(56) References Cited

U.S. PATENT DOCUMENTS

| | | | |
|---|---|---|---|
| 3,797,473 A | 3/1974 | Mutchler | |
| 4,055,745 A * | 10/1977 | Balaguer | H05B 3/0004 219/385 |
| 4,355,972 A * | 10/1982 | Stamper | A21B 1/48 432/148 |
| 4,357,522 A | 11/1982 | Husslein et al. | |
| 4,829,158 A * | 5/1989 | Burnham | F24C 15/325 126/21 A |
| 5,816,797 A | 10/1998 | Shoenfeld | |
| 6,462,311 B1 * | 10/2002 | Emiglio | A21B 1/22 219/391 |
| 6,722,872 B1 * | 4/2004 | Swanson | B29C 41/36 425/225 |
| 6,933,472 B1 | 8/2005 | Smith et al. | |

(Continued)

FOREIGN PATENT DOCUMENTS

WO WO8604978 8/1986

OTHER PUBLICATIONS

TeamBest Overview Presentation, Sep. 13, 2014.
(Continued)

*Primary Examiner* — Tu B Hoang
*Assistant Examiner* — Alba T Rosario-Aponte

(57) ABSTRACT

A warming oven includes a housing that forms a chamber and has a heat insulating material. A support member positioned within the chamber has a support surface. Heating elements are arranged within the chamber in an opposing relationship to the support member. The heating elements generate radiant heat towards the support member and have passages to heat an air flow through these passages and across the heating elements. An air circulator communicates with the chamber and includes a fan to generate the air flow, an exhaust to direct the air flow, and an intake to receive the returning air flow. A temperature sensor senses a temperature of the air flow. A controller communicates with the temperature sensor and selectively controls the air circulator and/or the heating elements to adjust the generated air flow or the heat output for temperature regulation. This temperature regulation can provide for an operating temperature.

22 Claims, 10 Drawing Sheets

(56) References Cited

U.S. PATENT DOCUMENTS

| | | | |
|---|---|---|---|
| 7,166,821 B2 | 1/2007 | Adamski | |
| 7,590,218 B2 | 9/2009 | Scherch et al. | |
| 8,957,350 B1* | 2/2015 | Juhl | A61M 5/44 |
| | | | 219/385 |
| 2002/0092842 A1* | 7/2002 | Loveless | F24C 7/10 |
| | | | 219/400 |
| 2005/0211696 A1* | 9/2005 | Adamski | A47J 39/00 |
| | | | 219/400 |
| 2008/0190300 A1* | 8/2008 | Adamski | A21B 1/22 |
| | | | 99/341 |
| 2009/0188915 A1* | 7/2009 | Noda | A21B 1/245 |
| | | | 219/757 |
| 2013/0004630 A1 | 1/2013 | McFadden | |
| 2014/0083309 A1 | 3/2014 | Reese et al. | |
| 2016/0282376 A1* | 9/2016 | Keller | G01N 1/312 |

OTHER PUBLICATIONS

AAPM 2014 trade show, Austin, TX, Jul. 20-23, 2014.
RSNA 2014 trade show, Chicago, IL, Nov. 30-Dec. 5, 2014.
North Sea Plastics website, www.northseaplastics.com/thermoplastic-ovens/index.asp, retrieved on Jul. 7, 2015.
MRC Lab website, www.mrclab.com/htmls/po350_thermoplastic_sheet_preheating_oven.aspx?c0=81314&bsp=76210, retrieved on Jul. 7, 2015.
International Search Report, PCT/US15/40738 (corresponding case), report dated Oct. 8, 2010, 7 pages.

\* cited by examiner

WARMING OVEN

BACKGROUND OF THE INVENTION

1. Field of the Invention

The present invention generally relates to warming devices, and in particular, to a warming oven for thermoplastic materials.

2. Description of Related Art

Various medical procedures are performed when a patient is immobilized. For example, certain radiation treatments implement a thermoplastic immobilization mask to prevent movement of the patient's head during radiation therapy. These thermoplastic masks can be warmed so that the thermoplastic material can be altered and adjusted. As an example, the mask is warmed so that it can be contoured in relation to the patient's head to provide a relatively precise fit.

Presently there are various warming devices on the market that can warm these masks. One example of a warming device is a warm water bath. When using the warm water bath, the mask is deposited within the warm water of the bath and is heated by the heat from the warm water. A possible drawback with the warm water bath is that it can be relatively messy and cumbersome when removing the thermoplastic mask from the warm water. Further, by having the thermoplastic mask warmed by the warm water, the mask can retain and exude a relatively harmful humidity level to sensitive equipment. As an example, sensitive equipment such as a Computed Tomography (CT) imaging machine can be harmed by this humidity level.

Another existing device for warming thermoplastic masks is a plate and cup warming device. Similar to the warm water bath, the plate and cup warming device also has certain drawbacks. For example, the plate and cup warming device is generally configured for installation into a kitchen cabinet. This configuration can limit the area and manner in which this device can be implemented. Further, the interior dimensions of the drawer of the plate and cup warming device may not be adequate in accommodating the relatively larger thermoplastic masks. For example, thermoplastic masks that have a size of 24 inches (in)×18 in (60.96 centimeters (cm)×45.72 cm) may not be accommodated by the drawer of the plate and cup warming device. Additionally, the plate and cup warming device is not traditionally considered for heating thermoplastic masks. Therefore it may not be feasible to warm a mask with the plate and cup warming device since the device is not configured for that operation.

Another warming device out on the market incorporates a silicone beating pad having a 1300 watts capacity, combined together with four relatively small computer fans for air circulation. The drawbacks for this device include the small heat capacity that is generated, which can cause this device to take a relatively extended time in reaching an appropriate operating temperature. Another drawback is that the unregulated flow from the computer fans can create uneven heating. Additionally, the lack of substantial insulation can cause the external surfaces of this warming device to get relatively hot. This can result in surfaces that are hot to the touch and heat losses that may extend process times.

Also for consideration is simply re-purposing an existing "convection oven" used in food preparation to process the thermoplastic masks. Similar to the previously mentioned devices, there are drawbacks with this approach as well. For example, standard convection ovens are typically not suitable due to the relatively low temperature generally required to process the thermoplastic mask. Further, uneven air temperatures are typically present in convection ovens throughout the interior of the oven. Generally speaking, a convection oven is often intended to operate at relatively higher temperatures and for a relatively longer process time than is acceptable for thermoplastic mask processing and preparation.

Therefore, it is desirable for a device that has an adequate process drawer size so as to accommodate the relatively larger thermoplastic masks, such as those masks that are about 24 in×18 in (60.96 cm×45.72 cm) plus clearance in size. Further, it is also desirable for a warming device that can process select support cushions which may have been pre-formed and may have a thickness of up to about four inches (10.16 cm). In addition, it is desirable for a device that can be brought to an appropriate operating temperature so as to provide for a relatively shorter time period to ready for use.

Additionally, it is desirable for a warming device that is capable of reducing the processing time of the thermoplastic mask. Further, it is desirable for a warming device that has a heating capacity that can be maximized when using a standard 15 amp (A) household current at 120 volts alternating current (VAC) or at 8 A European Union (EU) current at 220 VAC. Furthermore, it is desirable for a device to have a temperature controller to provide for precise temperature control.

Thus, a warming oven for addressing the aforementioned problems is desired.

SUMMARY OF THE INVENTION

A warming oven includes a housing that forms a chamber to receive an object to be heated. The housing is associated with a heat insulating material that is adapted to reduce heat transfer from the chamber. Additionally, the warming oven includes a support member which can be positioned within the chamber. The support member has a support surface adapted to receive and support the object that is to be heated. Further, a plurality of heating elements are arranged, such as in a spaced relation, within the chamber and in an opposing relationship to the support member. The plurality of heating elements are adapted to generate a radiant heat in a direction towards the support member. Further, the heating elements have passages to heat an air flow directed through these passages and across the corresponding heating elements.

The warming oven also includes an air circulator in communication with the chamber. The air circulator includes a fan with an accompanying fan housing to generate the air flow in the chamber, an exhaust to direct the air flow from the air circulator into the chamber, and an intake to receive the air flow returning to the air circulator from the chamber. This air circulator creates a flow path for the generated air flow through the chamber from the exhaust to the intake. The exhaust directs the generated air flow along the flow path in a first direction across the heating elements through the passages of the heating elements to heat the air flow. The heated air flow then circulates along the flow path in a second direction toward the air circulator to mix the heated air flow with the radiant heat generated by the heating elements. This mixing of the heated air flow with the radiant heat can provide a substantially uniform operating temperature in the chamber to heat the object.

The warming oven further includes a temperature sensor for sensing a temperature of the air flow in the chamber. Additionally, a controller communicates with the temperature sensor to receive the sensed temperature of the air flow. Based on the received sensed temperature, the controller selectively controls at least one of the air circulator and the heating elements to adjust at least one of the generated air flow or the heat output of the heating elements for temperature regulation within the chamber. This temperature regulation provides for a selected substantially uniform operating temperature so that the object can be warmed appropriately.

BRIEF DESCRIPTION OF THE DRAWINGS

Unless otherwise indicated, similar reference characters denote corresponding features consistently throughout the attached drawings.

DETAILED DESCRIPTION OF THE INVENTION

Figure 1:
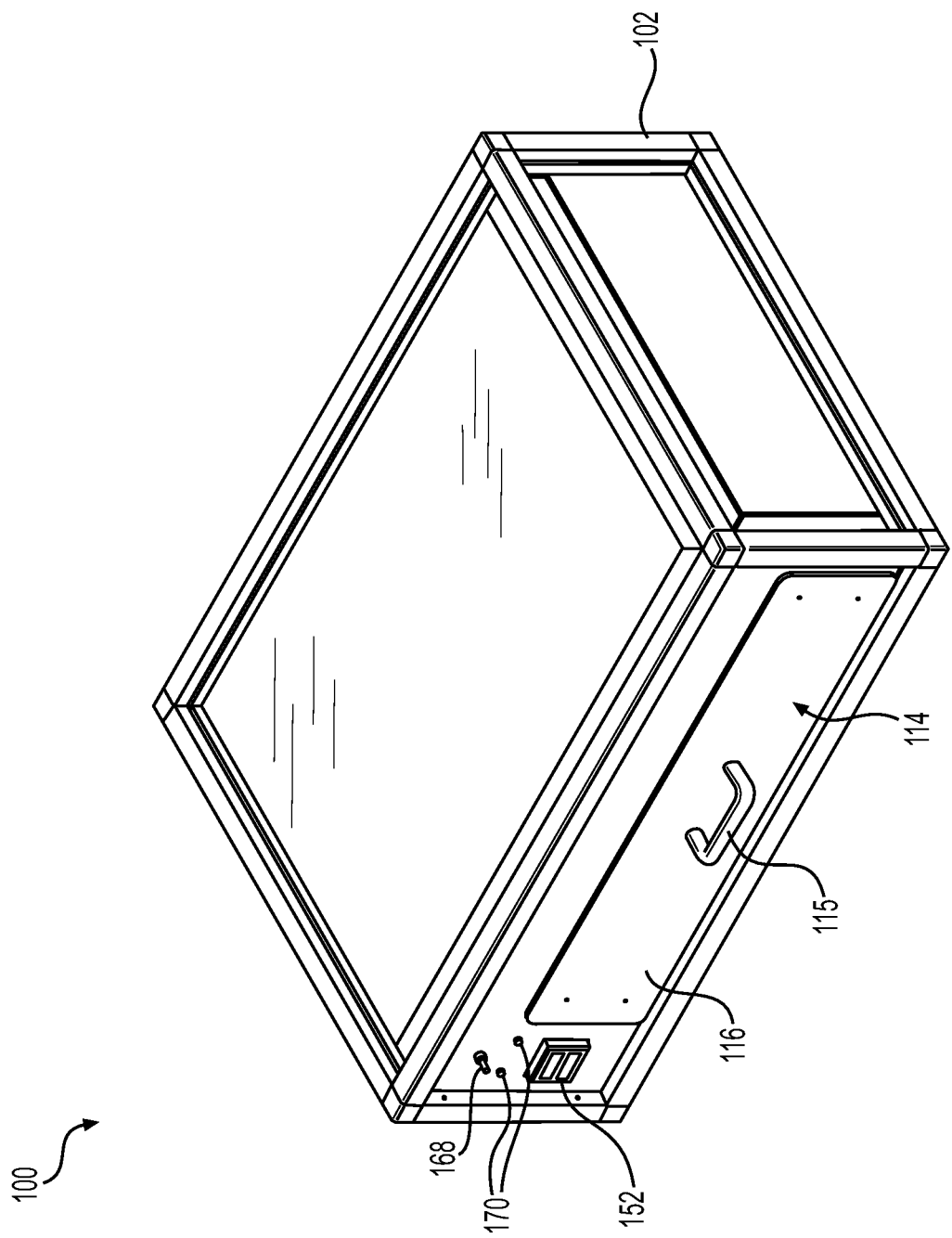
FIG. 1 is a perspective view of a warming oven according to the present invention.

The warming oven allows for an object, such as a thermoplastic mask used in patient immobilization, to be warmed. The warming oven accomplishes this warming through an arrangement in which a plurality of heating elements are arranged together in an opposing relationship to a support member that supports the thermoplastic mask. An air circulator generates an air flow implemented by a fan with an accompanying fan housing. This generated air flow is carried across the plurality of heating elements and throughout the chamber. A temperature sensor within the chamber senses the temperature of the air flow in the chamber. Based on this sensed temperature, a controller selectively controls at least one of the air circulator and the heating elements to adjust at least one of the generated air flow or a heat output of the heating elements for temperature regulation within the chamber to provide for a selected substantially uniform operating temperature.

Referring to FIGS. 1-10, a warming oven 100 is disclosed. The warming oven 100 includes a housing 102 which acts an enclosure that forms a chamber 104. This housing can be of any suitable arrangement or materials, depending on the user's needs. For example, the housing 102 can be an exposed frame of an extruded shaped aluminum material with removable panels. Another possibility is that the housing 102 is a double clam shell base/cover assembly. The housing 102 can be used or provided with either choice of enclosure, for example. Points of consideration are that the exposed frame enclosure can be relatively costly to manufacture. On the other hand, the clam shell enclosure can be both relatively cost effective and relatively easier to assemble. Further, the housing 102 can come in multiple pieces, or have a smooth surface, or include a stainless steel material, or it can be a painted enclosure.

The chamber 104 that is formed by the housing 102 is adapted to receive an object 106 that is to be heated. The object 106 can be any object that can be warmed and fits the user's needs. For example, the object 106 can be a thermoplastic material, such as a thermoplastic mask used for patient immobilization in certain radiation treatment therapies. The thermoplastic mask can be warmed while within the chamber 104 so that it can become malleable. Once removed from the chamber 104, the thermoplastic mask can be contoured to fit a portion of a patient's body. For example, the thermoplastic mask can be contoured to fit onto a patient's face so that the patient's head is immobilized during a radiation therapy treatment. The thermoplastic mask that can be heated by the warming oven 100 can be various shapes and sized. For example, the thermoplastic mask can be up to about 24 in×18 in (60.96 cm×45.72 cm) plus clearance in size. Additionally, the object 106 can be other medical materials or devices, simply depending on the user's needs. For example, the object 106 can be a support cushion having a thickness of up to about four inches. Also, embodiments of the warming oven 100 can have other suitable applications for warming objects in other medical or non-medical applications, for example, and should not be construed in a limiting sense.

Continuing with the housing 102, a heat insulating material 108 is associated with the housing 102. The heat insulating material 108 can be a number of various materials that allow for heat insulation during a warming process. For example, the heat insulating material 108 can be about a one inch (2.54 cm) thick fiberglass insulation material, as can be combined together with a reflective foil backing, applied on all sides, top and bottom of the chamber 104. By placing the heat insulating material 108 on all sides, top and bottom of the chamber 104, it can allow the chamber 104 to be relatively fully insulated. Further, it can allow for the warming oven 100 to limit waste heat. As an example for this, the heat insulating material 108 can allow the housing 102 to remain cool to the touch, which indicates that heat transfer from the chamber 104 is reduced. Other materials can be suitable for selection of the heat insulating material 108, depending on the user's needs.

Figure 2:
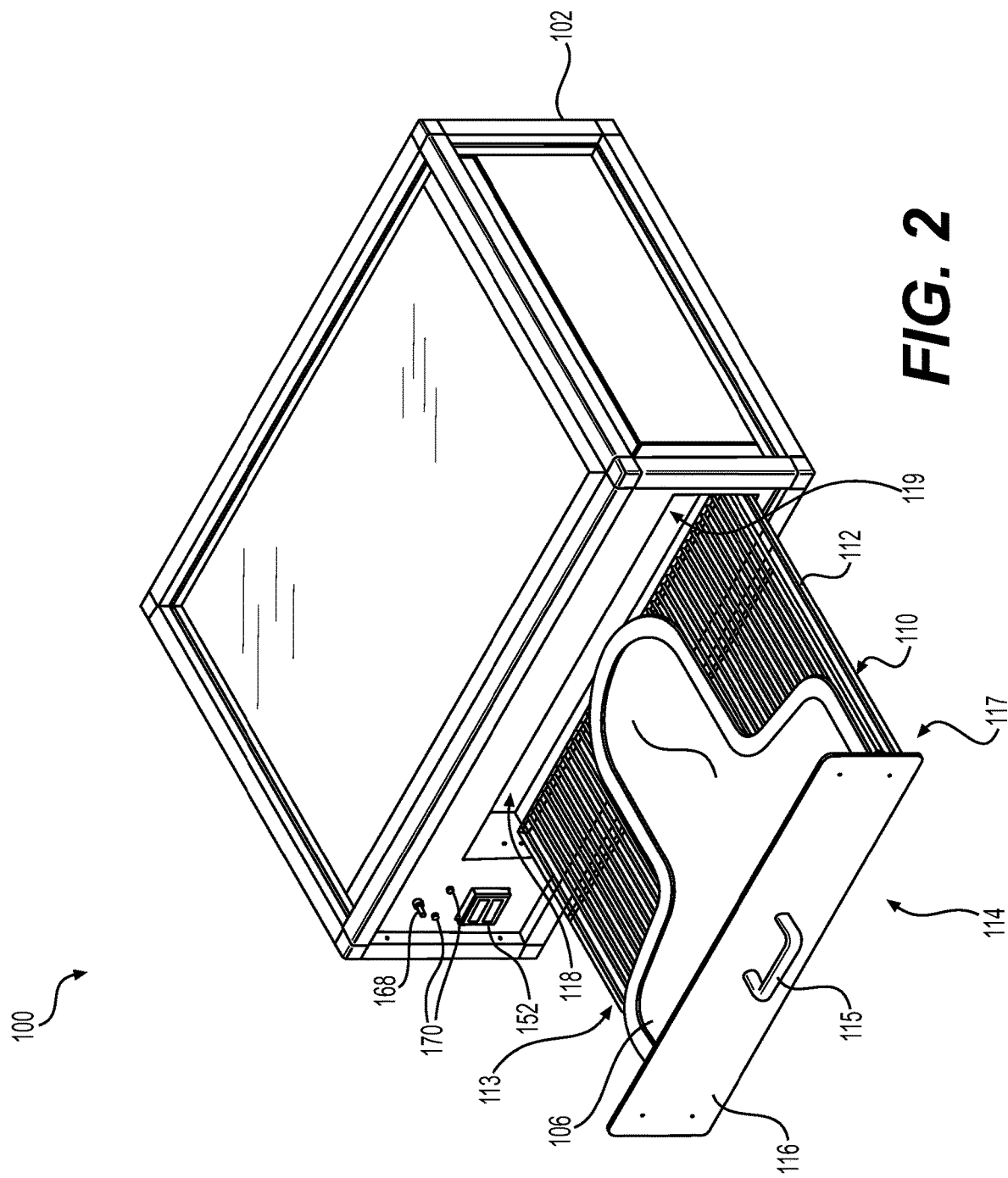
FIG. 2 is an environmental view of a thermoplastic mask supported by a support member of a warming oven according to the present invention.
Figure 6:
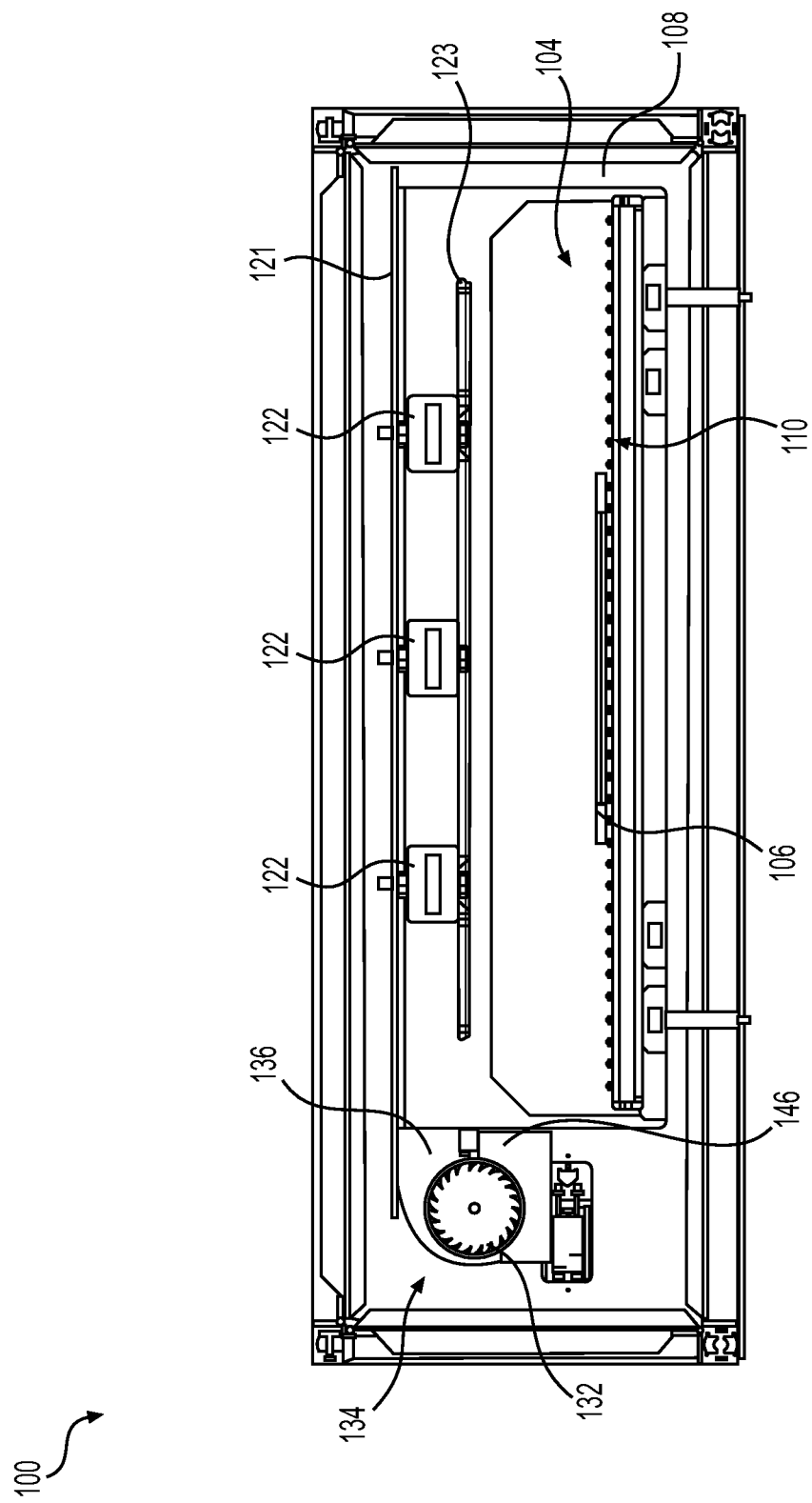
FIG. 6 is a sectional front view of a warming oven according to the present invention.
Figure 7:
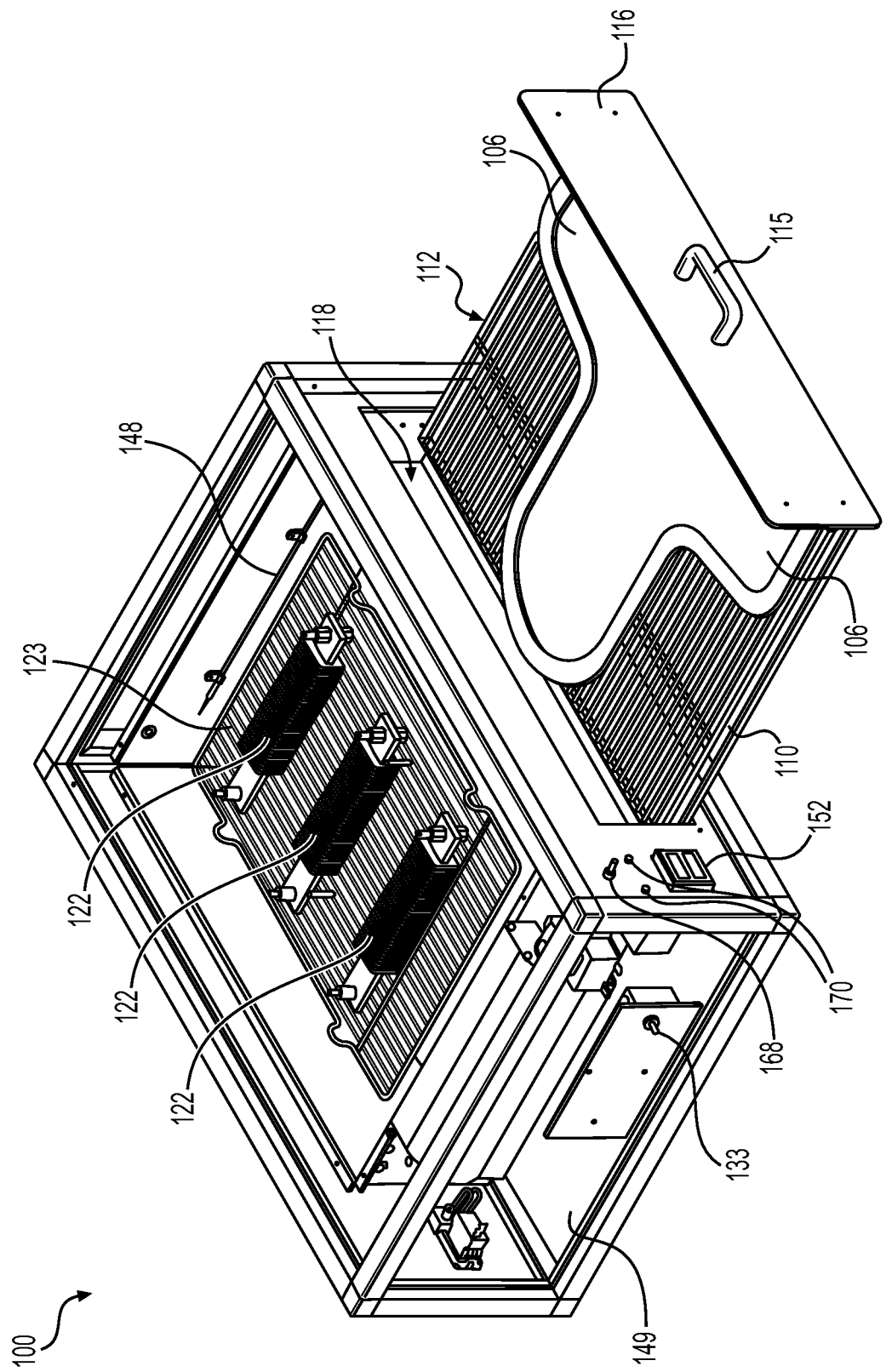
FIG. 7 is a sectional environmental view of embodiments of a plurality of heating elements and a thermoplastic mask in use with a warming oven according to the present invention.

As shown in FIGS. 2, and 6-7, the object 106 can be positioned within the chamber 104 by being supported by a support member 110. The support member 110 is adapted to be positioned within the chamber 104, as specifically illustrated in FIG. 6. The support member 110 includes a support surface 112, which is adapted to receive and support the object 106 that is to be heated. The support member 110 and the accompanying support surface 112 can come in a grid configuration or another other suitable arrangement that allows for the object 106 to be supported. If a thermoplastic mask is selected as the object 106, the support member 110 and the accompanying support surface 112 can be of a size that accommodates the relatively larger sized thermoplastic masks. As an example the support member 110 can accommodate masks about 24 in×18 in (60.96 cm×45.72 cm) plus clearance in size or even support cushions having a thickness of up to about four inches. Additionally, the support surface 112 of the support member 110 can be made of or coated with a polytetrafluoroethylene (PTFE) material to allow for relatively easier removal of the object 106 from the support surface 112.

As illustrated in FIGS. 2 and 5-7, the support member 110 can be selectively moved in relation to and within the chamber 104. The selective movement of the support member 110 can be accomplished by the support member 110 being in connection with a movable member 114. The movable member 114 can be placed into an open position, as illustrated in FIGS. 2 and 7. In the open position, the object 106 can be positioned outside the chamber 104. Further, in this open position, the object 106 can be removed from the warming oven 100.

Figure 5:
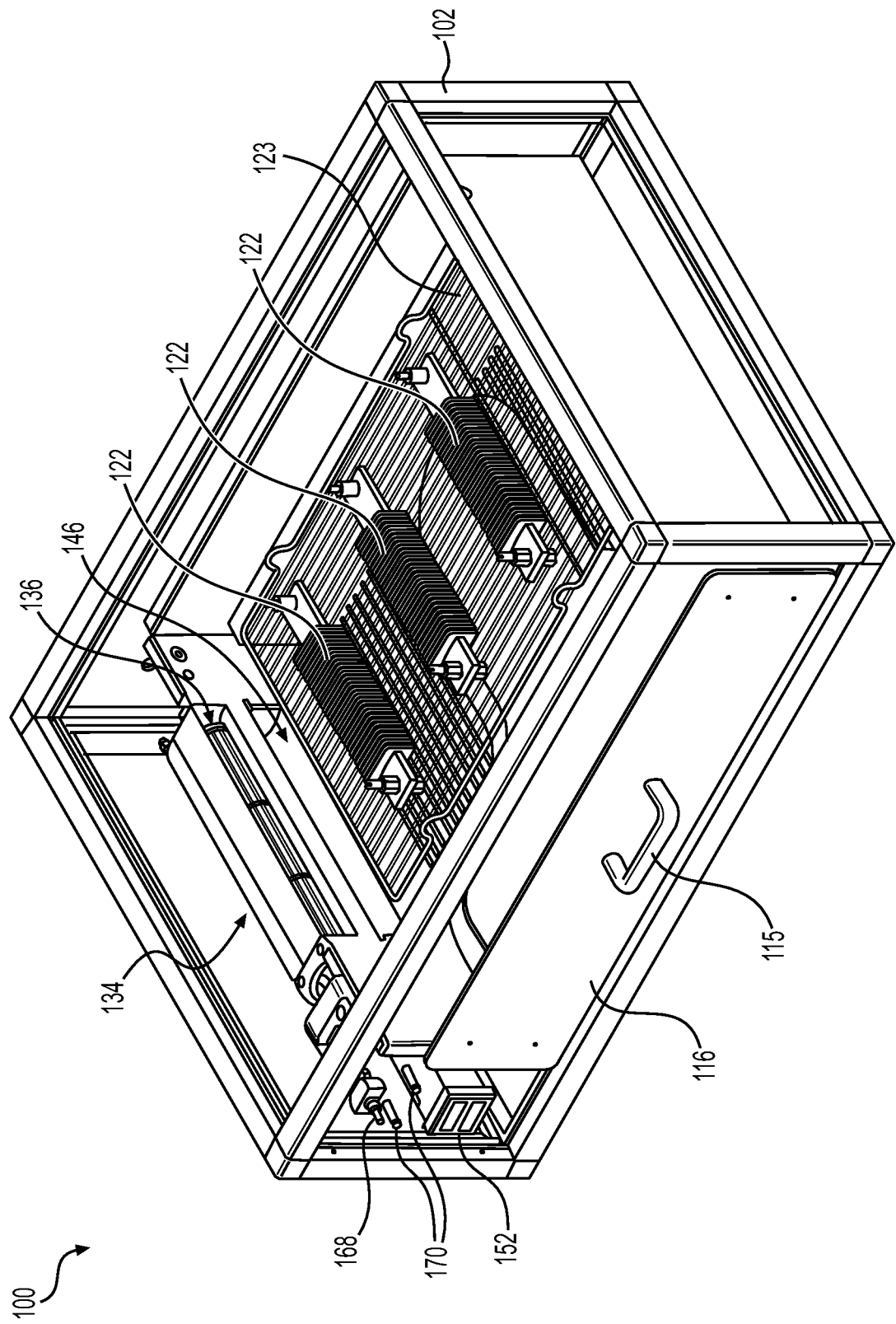
FIG. 5 is a sectional perspective view illustrating embodiments of a plurality of heating elements of a warming oven according to the present invention.

As illustrated in FIGS. 5 and 6, the movable member 114 can also be placed into a closed position. In the closed position, the object 106 is positioned within the chamber 104. The closed position is the suitable position during operation of warming oven 100. Therefore, the movable member 114 drives the selective movement of the support member 110 in and out of the chamber 104, which allows for the support member 110 to be positioned in and out of the housing 102 so that the object 106 can be heated in the chamber 104.

The movable member 114 can be any suitable member, such as a process drawer 113, such as can have a handle 115, among other examples. If the process drawer 113 is selected as the movable member 114, than the movable member 114 can include an arrangement with a front flange 116 at a front end 117 of the process drawer 113 as can provide a front member of the process drawer 113. Further, the arrangement can also include the movable member 114 having a rear flange 118 positioned near an opposite end 119 of the process drawer 113 that is adapted to restrict access to an interior of the chamber 104. The front flange 116 is illustrated in FIGS. 1, 2, 5, and 7. The rear flange 118 is illustrated in FIG. 2. The rear flange 118 can prevent contact of the heating elements 122 or a fan 132 by the user. Further, a guard 123 is installed just beneath the plurality of heating elements 122 to additionally prevent contact by the user.

Figure 3:
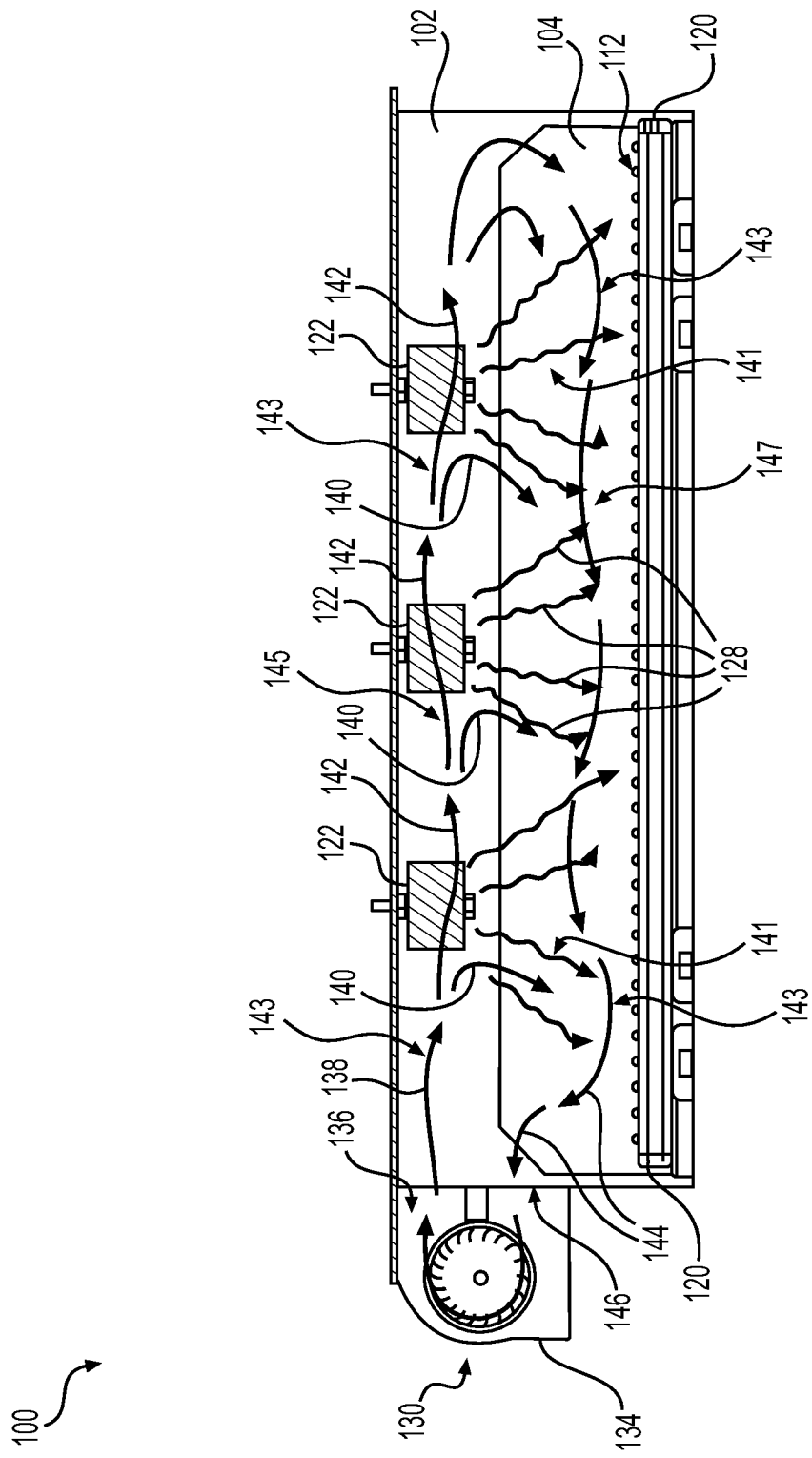
FIG. 3 is a cross-sectional view illustrating a generated air flow pattern of a warming oven according to the present invention.

In addition to the front flange 116 and the rear flange 118, the movable member 114 can further include downturned flanges 120 at a left edge and a right edge of the process drawer 113. These downturned flanges 120 allow facilitation of air flow across the chamber 104. The downturned flanges 120 are illustrated in FIG. 3. Therefore, if the movable member 114 is the process drawer 113, the process drawer 113 is arranged to facilitate a substantially full right to left cross flow of the recirculated air across the chamber 104 that is relatively low to a drawer base surface of the process drawer 113, for example. This air flow can be facilitated by incorporating the front flange 116 and the rear flange 118 at nearly a chamber height of the chamber 104 and with the downturned flanges 120 at the left and right edges of the drawer, for example.

The movable member 114 can include a movement member that allows for the movement of the movable member 114 to allow for the selective movement of the support member 110, such as the movable member sliding in and out of the chamber 104. The movement member can be any suitable member that allows for movement, such as a rack and pinion arrangement, or wheels, among other examples. The movement member can be positioned on a bottom surface of the movable member 114 to allow not only for movement but to also provide support for the movable member 114 while in the open position and in the closed position. Further, the movement member is such that it can enhance the longevity of the movable member 114. The movement member can also be a segmented arrangement with segmented slides laid flat with a main slide segment fastened to a base of the housing 102 and another segment attached to an underneath of the movable member 114.

The warming oven 100 further includes a plurality of heating elements 122, as illustrated in FIGS. 3-8. The heating elements 122 can be arranged in a spaced relation within the chamber 104. Further, the heating elements 122 are also in an opposing relationship to the support member 110. Each heating element 122 out of the plurality of heating elements 122 can be an electric resistance finned strip heater having finned strips 124 to generate heat, such as a radiant heat 128. The heating elements 122 are un-shrouded, except for the guard 123, shown as a protective grate in FIGS. 5-7. The un-shrouded placement of the heating elements 122 can provide the radiant heat 128 to relatively accelerate the heating of the chamber 104 and can facilitate air flow within the chamber 104 and adjacent to a surface of the object 106.

Additionally, the heating elements 122 can be positioned on a reflective ceiling 121 of the chamber 104, such as can include a reflective foil. In this arrangement the plurality of heating elements 122 are adapted to generate the radiant heat 128 in a direction toward the support member 110, as illustrated in FIG. 3. Therefore, the heating elements 122 can be positioned between the reflective ceiling 121 and the guard 123. The heating elements 122 can be alternately placed below the support member 110 so as to provide a resultant increase in height of the warming oven 100. In such an instance the movable member 114 would be an open flow-through design to permit passage of a heated air. Additionally, a fan air path would also be reversed to flow from the bottom up through the chamber 104.

As shown in FIGS. 3-6, an air circulator 130 is in communication with the chamber 104. The air circulator 130 includes a fan 132 with an accompanying fan housing 134 to generate an air flow 138 in the chamber 104. The fan housing includes an exhaust 136 and an intake 146. The fan 132 with accompanying fan housing 134 can be any suitable commercially available fan and fan housing combination, such as an extra wide squirrel cage fan. If the extra wide squirrel cage fan is selected, a wide even flow of air can be generated by the inherent design of this fan type. For example, the fan 132 and accompanying fan housing 134 can be a 12 in (30.48 cm) wide squirrel cage.

Figure 8:
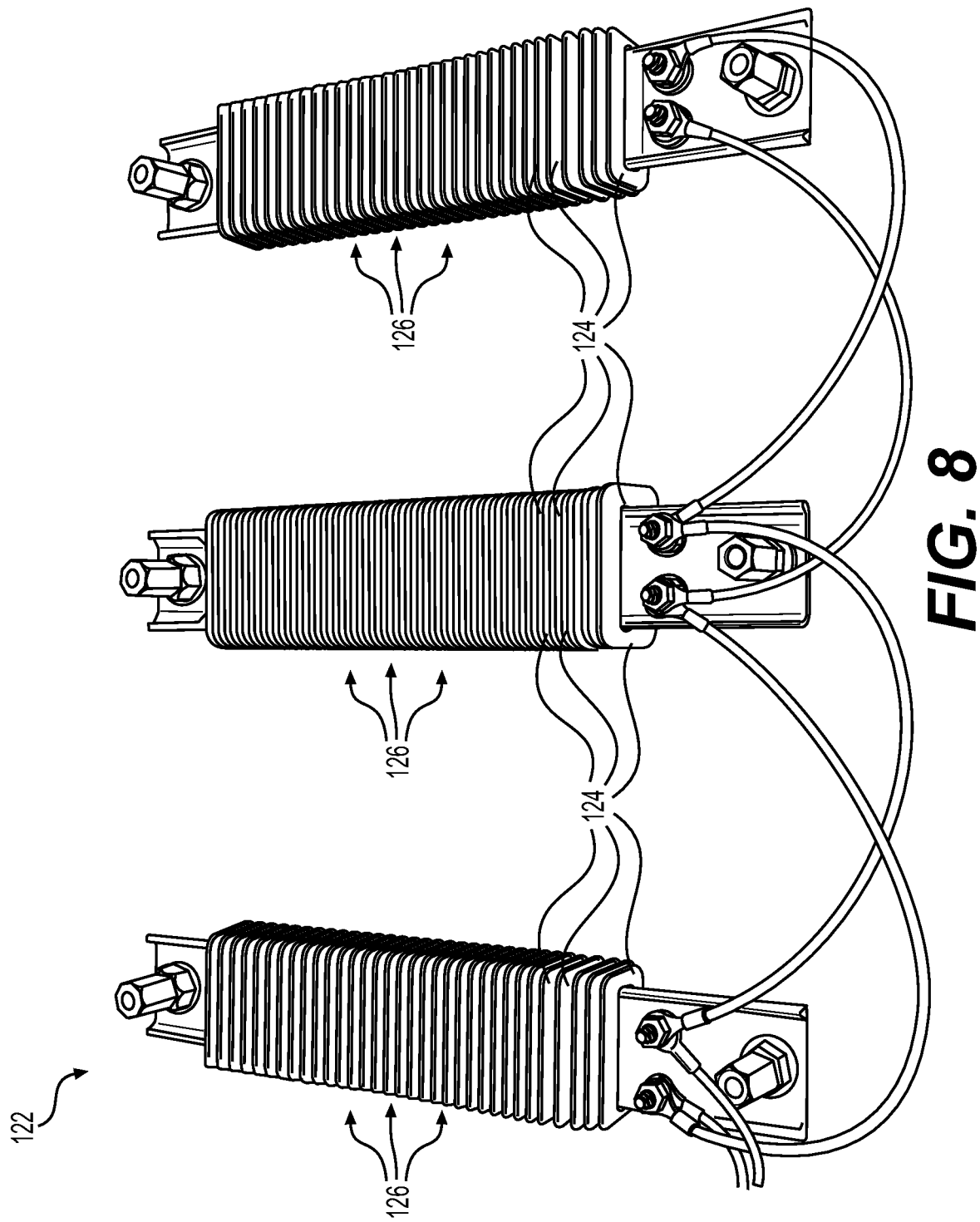
FIG. 8 is a perspective view of embodiments of a plurality of heating elements for a warming oven according to the present invention.

As illustrated in FIG. 3, the exhaust 136 directs the generated air flow 138 from the air circulator 130 into the chamber 104. The finned strips 124 of each heating element 122, such as the adjacent ones of the finned strips 124, can form a corresponding passage 126 (FIG. 8) to allow the generated air flow 138 to flow from one heating element 122 to an adjacent heating element 122. Further, as the generated air flow 138 flows through the passages 126, the generated air flow 138 is heated as it passes through the corresponding passages 126, with this heated air flow 142 circulating along a flow path 143, as shown in FIGS. 3 and 8. Thus, the passages 125 between the finned strips 124 allow for the generated air flow 138 to be heated when the air flow 138 is directed through the passages 126 and across the corresponding heating elements 122. In summary, the fan 132 and accompanying fan housing 134 can be used to draw a warmed air or a pre-warmed air through a calibrated orifice, such as the intake 146, and then to expel this warmed air or pre-warmed air out through the exhaust 136 as the generated air flow 138 across the finned strips 124 of the heating elements 122.

As shown in FIG. 3, the exhaust 136 directs the generated air flow 138 along the flow path 143 in a first direction 145 across the heating elements 122 through the passages 126 of the heating elements 122 to heat the generated air flow 138. Further, the heated air flow 142 circulates along the flow path 143 in a second direction 147 toward the air circulator 130 to mix the heated air flow 142 with the radiant heat 128 generated by the heating elements 122. In addition to this, the plurality of heating elements 122 can divert a portion of the generated air flow 138 from the flow path in a direction 141 towards the support member 110 by the finned strips 124 of the heating elements 122. This diversion of the generated air flow 138 is illustrated in FIG. 3. Diverting the generated air flow 138 can create turbulence in the generated air flow 138 in a direction toward the support member 110. This turbulence in the generated air flow 138 is represented as a turbulent air flow 140 in FIG. 3.

The turbulent air flow 140 can further provide homogenization of e heated air flow 142 within the chamber 104 during a mixing of the heated air flow 142 with the radiant heat 128. This mixing of the heated air flow 142 with the radiant heat 128 can provide for a substantially uniform operating temperature in the chamber 104 to heat the object 106. In the case of a thermoplastic mask being the object 106, the uniform operating temperature can be about 165 degrees Fahrenheit (° F.) (73.89 degrees Centigrade (° C.)). The turbulent air flow 140 can assist in achieving this selected substantially uniform operating temperature of about 165° F. (73.89° C.) within the chamber 104. It is also desirable, in addition to the selected substantially uniform operating temperature of about 165° F. (73.89° C.), that the warming oven takes a time period of about 15 minutes to warm up from "cold" to operating temperature, referred to as a heat up time, to achieve this substantially uniform operating temperature of about 165° F. (73.89° C.) within the chamber 104. If a thermoplastic mask is the object 106, the thermoplastic mask can be processed in as little as about 10 minutes, for example.

As stated previously, the exhaust 136 of the fan housing 134 directs the generated air flow 138 from the air circulator 130 into the chamber 104. The reverse flow of the heated air 142 back across the chamber 104 eventually flows into the intake 146 of the fan housing 134. Thus, the air circulator 130 allows for the flow path 143 to be created that allows the generated air flow 138 to flow through the chamber 104 from the exhaust 136 to the intake 146. In summary, the air within the chamber 104 flows through the chamber 104 and then reverses flow to flow back across the chamber 104 so that a substantially thorough homogenization of the heated air 142 can occur so that all corner areas of the chamber 104 are maintained at the same or substantially the same temperature.

It should be noted that any number of heating elements 122 can be implemented with the warming oven 100, depending on the user's needs. Further, each heating element 122 can have a differing or same capacity value as another heating element 122. For example, if three heating elements 122 are implemented, one heating element 122 can have a capacity of 725 watts (W), while the other remaining two heating elements 122 can have a capacity of 500 W each, as can depend on the use or application.

It is desirable that the higher capacity heating element 122, for example the heating element 122 that has a capacity of 725 W, is placed closest to the air circulator 130, and specifically closest to the fan 132. Thus, lower capacity heating elements 122, such as heating elements 122 having 500 W capacities, would be relatively farther away from the air circulator 130 compared to a 725 W capacity heating element 122. To summarize, in a desirable arrangement of the heating elements 122 in the chamber 104, at least one of the heating elements 122 has a higher capacity for heat output than at least one other of the plurality of heating elements 122 so as to provide a higher heat output than at least one other of the plurality of heating elements to adjust for heat loss in the generated air flow 138 along the flow path 143.

Figure 4:
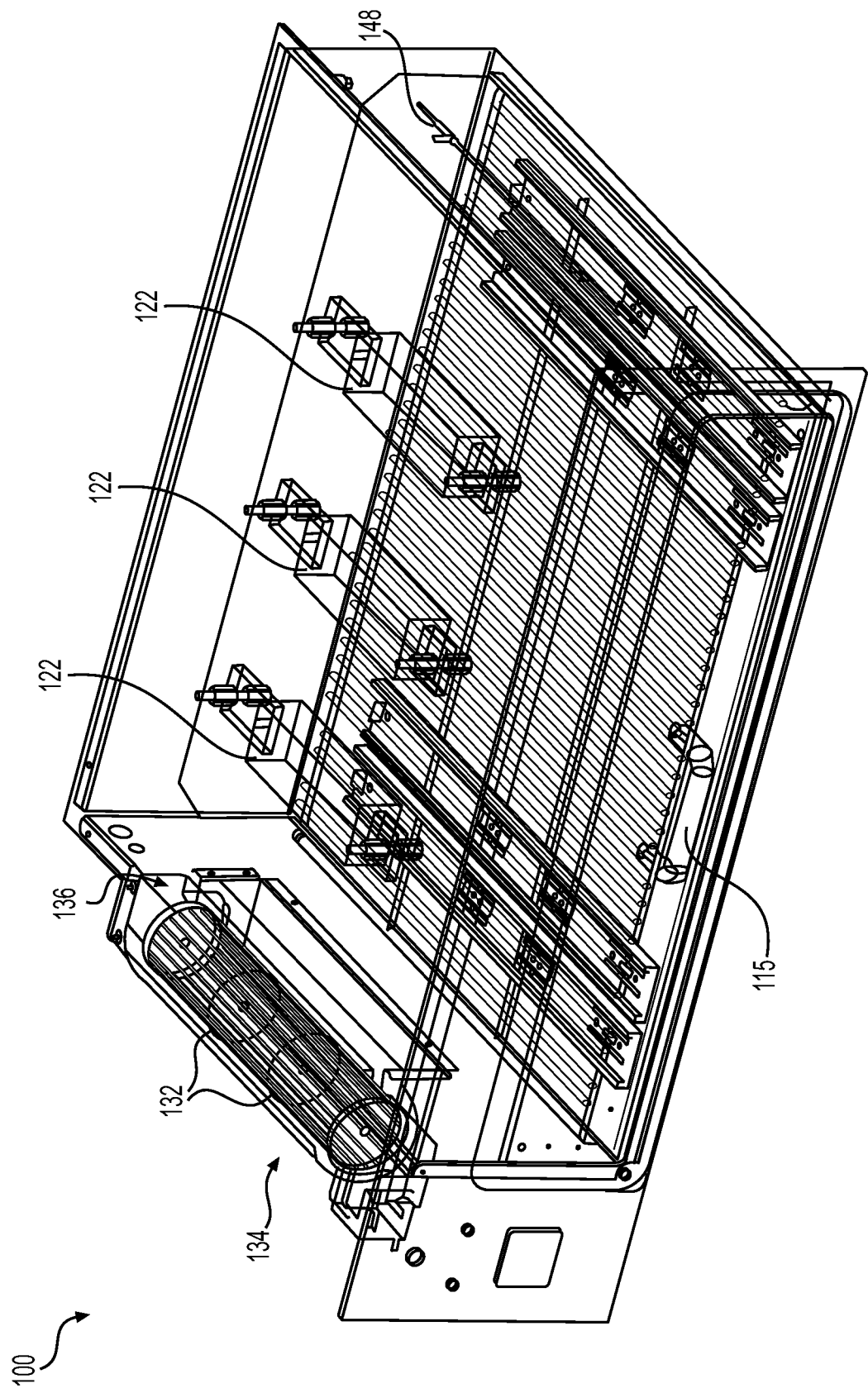
FIG. 4 is a sectional perspective view illustrating embodiments of a fan and a support member of a warming oven according to the present invention.

The warming oven 100 further includes a temperature sensor 148 to sense a temperature of the air flow in the chamber 104, such as the heated air flow 142. As illustrated in FIGS. 4 and 7, the temperature sensor 148 can be positioned within the chamber 104 in an opposing relationship to the air circulator 130, desirably at an opposite end of the chamber 104 from the air circulator 130. Additionally, the temperature sensor 148 can be positioned in a horizontal orientation. Further, the temperature sensor 148 can be any suitable temperature sensor, for example, a thermocouple. Regarding the thermocouple, a relatively long and/or thin thermocouple can be used for sensing air temperature as opposed to a relatively shorter, fatter sensor that is intended to be submersed in water, for example.

Figure 9:
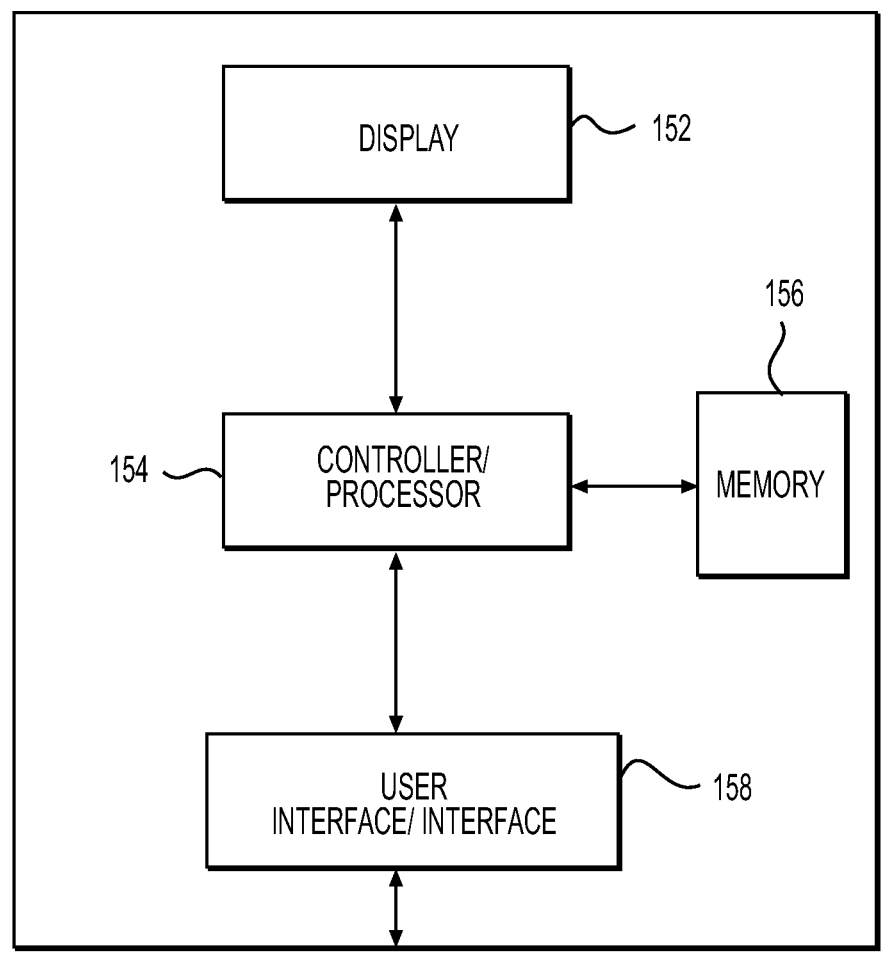
FIG. 9 is a schematic illustrating embodiments of a controller for a warming oven according to the present invention.

The warming oven 100 also includes an exemplary controller 150, as illustrated in FIG. 9. The controller 150 is in communication with the temperature sensor 148 to receive the sensed temperature of the air flow. Based on this received sensed temperature from the temperature sensor 148, the controller 150 selectively controls at least one of the air circulator 130 and the heating elements 122 to adjust at least one of the generated air flow 138 or the heat output of the heating elements 122 for temperature regulation within the chamber 104. This temperature regulation within the chamber 104 can provide the selected substantially uniform operating temperature, which as mentioned above, is about 165° F. (73.89° C.) for when a thermoplastic mask is selected as the object 106. The temperature sensor 148 provides a closed loop operation with the controller 150 to maintain the temperature inside the chamber 104 to a relatively precise degree. The controller 150 and its accompanying components can be located within an electrical cavity 149 within the housing 102, as shown in FIG. 7. This electrical cavity 149 can be below the air circulator 130, or any other suitable location.

The controller 150 can include a proportional-integral-derivative (PID) controller, such as can include an Athena® Series 16C Temperature/Process Controller, for example, in communication with the plurality of heating elements 122, such as through a solid state relay (SSR), for example. The controller can be a control system with a self-contained analog controller and no SSR. Regardless of which type of controller 150 is selected, the same or other suitable temperature sensor 148 can be used. Another controller configuration can include a countdown to off timer to automatically turn off the plurality of heating elements 122 of the warming oven 100 at a predetermined time. This timer can be pre-set. However, it also can be configured for user adjustability. Regardless of which type of controller 150 is selected, all models can desirably incorporate a movable member 114 sense switch that can remove or adjust power from the plurality of heating elements 122 and the air circulator 130, specifically the fan 132, while the heat insulating material 108 can facilitate preserving the warm air inside the chamber 104 when the movable member 114 is in the open position, for example brief periods such as loading and unloading. Further, all circuit wiring can be done by a custom designed or other suitable wiring harness.

The selective control of the air circulator 130 by the controller 150 can occur by the selective control of a fan speed regulator 133, illustrated in FIG. 7. The fan 132 is desirably controlled by the fan speed regulator 133 in order to present a low velocity flow of air across the plurality of heating elements 122. The controller 150 can be adjusted to provide the fan with about 90 volts alternating current (VAC), which has been found to be a repeatable parameter for best results during experimentation, for example. Therefore, the controller 150 through selective control of the fan speed regulator 133, sets the fan speed of the fan 132, and thus sets the air flow, so as to enhance the facilitation of substantially even heating throughout the chamber 104 within the desired about 15 minute heat up time, for example. The fun speed regulator 133 can also be manually set with the use of a digital voltmeter (DVM) or can be set with the use of an analog voltmeter. The best perceived fan speed/air flow is a function of the alternating current (AC) input voltage to a fan motor associated with the fan 132. The fan voltage range to achieve the desired fan speed is about 85 VAC to 95 VAC, with the optimal setting at 90 VAC, for example.

FIG. 9 illustrates a generalized controller 150 for selectively controlling the operation of the warming oven 100. It should be understood that the generalized controller 150 may represent, for example, a stand-alone computer, computer terminal, portable computing device, networked computer or computer terminal, or networked portable device. Data may be entered into the generalized controller 150 by the user via any suitable type of user interface 158, and may be stored in a computer readable memory 156, which may be any suitable type of computer readable and programmable memory. Calculations are performed by a controller/processor 154, which may be any suitable type of computer processor, and may be displayed to the user on a display 152, which may be any suitable type of computer display, such as a liquid crystal display (LCD) or a light emitting diode (LED) display, for example.

The controller/processor 154 may be associated with, or incorporated into, any suitable type of computing device, for example, a personal computer or a programmable logic controller (PLC) or an application specific integrated circuit (ASIC). The display 152, the controller/processor 154, the memory 156, and any associated computer readable media are in communication with one another by any suitable type of data bus, as is well known in the art.

Examples of computer readable media include a magnetic recording apparatus, non-transitory computer readable storage memory, an optical disk, a magneto-optical disk, and/or a semiconductor memory (for example, RAM, ROM, etc.). Examples of magnetic recording apparatus that may be used in addition to memory 156, or in place of memory 156, include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Figure 10:
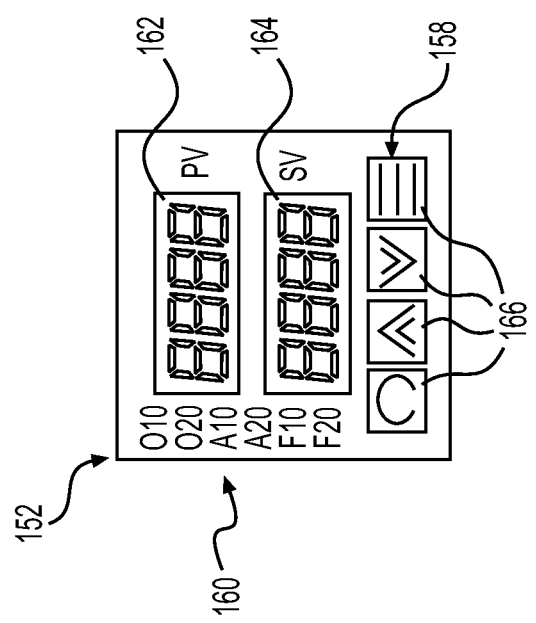
FIG. 10 is a front view of embodiments of a display for a controller for a warming oven according to the present invention.

Referring to FIG. 10, the display 152 is illustrated. In addition to the display, several buttons or operational elements of the user interface 158 are shown. For example, device operation indicators 160 of the controller 150 are shown. Further, a process value indicator 162, a set value indicator 164, and user input keys 166 are also shown. If an analog style controller is implemented, a standalone temperature display is provided to indicate the process temperature to the user. As illustrated in FIG. 5, above the display 152 can be positioned a power switch 168 to power the warming oven 100 and also operation indicators 170, which can indicate power and heat. It should also be noted that in additional embodiments the PID temperature controller can be replaced by an LED temperature display and a dial temperature setting potentiometer as can be utilized in conjunction with the operation indicators 170 and the power switch 168, for example. It should be noted that the controller 150 and the user interface 158 can provide for a control arrangement to allow the user to select and set the appropriate temperature from ambient to about 180° F. (82.22° C.), for example.

It is to be understood that the present invention is not limited to the embodiments described above, but encompasses any and all embodiments within the scope of the following claims.

I claim:

1. A warming oven, comprising:
a housing, the housing forming a chamber to receive an object to be heated, the housing having a heat insulating material adapted to reduce heat transfer from the chamber;
a support member, the support member adapted to be positioned within the chamber and having a support surface adapted to receive and support the object to be heated;
a plurality of heating elements, the heating elements being arranged within the chamber and in an opposing relationship to the support member, the plurality of heating elements adapted to generate radiant heat in a direction toward the support member and having passages to heat an air flow directed through the passages across the corresponding heating elements;
an air circulator in communication with the chamber, the air circulator including a fan to generate the air flow in the chamber, an exhaust to direct the air flow from the air circulator into the chamber and an intake to receive the air flow returning to the air circulator from the chamber, the air circulator creating a flow path for the generated air flow through the chamber from the exhaust to the intake, the exhaust directing the generated air flow along the flow path in a first direction across the heating elements through the passages of the heating elements to heat the air flow, the plurality of heating elements being adapted to divert a portion of the air flow in the first direction from the flow path in the direction toward the support member to directly engage and mix the diverted portion of the air flow with the air flow in a second direction toward the air circulator to create turbulence in the heated air flow circulating along the flow path in the second direction toward the air circulator to mix the heated air flow and the radiant heat generated by the heating elements with the diverted portion of the air flow in the flow path to provide turbulent heated air to facilitate a uniform operating temperature and uniform heating in the chamber to heat the object, the generated air flow by the air circulator in the flow path directly engaging and mixing with the diverted portion of the air flow from the plurality of heating elements generating turbulent heated air flow across the object to be heated to provide turbulent heated air to directly impinge upon the object to be heated;
a temperature sensor to sense a temperature of the air flow in the chamber; and a controller, the controller in communication with the temperature sensor to receive the sensed temperature of the air flow, and based on the received sensed temperature, the controller selectively controlling at least one of the air circulator or the heating elements to adjust at least one of the generated air flow or the heat output of the heating elements for temperature regulation within the chamber to facilitate a selected uniform operating temperature.

2. The warming oven according to claim 1, wherein the heat insulating material is a fiberglass material combined together with a reflective foil.

3. The warming oven according to claim 1, wherein the support surface of the support member comprises a polytetrafluoroethylene (PTFE) material.

4. The warming oven according to claim 1, wherein the support member is selectively movable within the chamber and the support member is in communication with a movable member to drive the selective movement of the support member in and out of the housing to position the object to be heated within the chamber.

5. The warming oven according to claim 4, wherein the movable member is a process drawer.

6. The warming oven according to claim 5, wherein the process drawer comprises an arrangement of a front flange at a front end of the process drawer to provide a front member of the process drawer and a rear flange positioned near an opposite end of the process drawer adapted to restrict access to an interior of the chamber together with downturned flanges at a left edge and a right edge of the process drawer to facilitate air flow across the chamber.

7. The warming oven according to claim 1, wherein the object includes a thermoplastic material.

8. The warming oven according to claim 1, wherein each heating element out of the plurality of heating elements is an electric resistance finned strip heater having finned strips to generate heat, wherein adjacent ones of the finned strips form a corresponding passage to heat the generated air flow through the corresponding passages circulating along the flow path.

9. The warming oven according to claim 1, wherein at least one of the heating elements has a higher capacity for heat output than at least one other of the plurality of heating elements to provide a higher heat output than at least one other of the plurality of heating elements to adjust for heat loss in the generated air flow along the flow path in facilitating the uniform operating temperature in the chamber.

10. The warming oven according to claim 9, wherein the at least one higher capacity heating element is positioned closest to the air circulator relative to other of the plurality of heating elements in facilitating the uniform operating temperature in the chamber.

11. The warming oven according to claim 10, wherein the plurality of heating elements divert the portion of the generated air flow from the flow path in the direction toward the support member to create the turbulence in the air flow in the direction toward the support member to provide homogenization of the heated air within the chamber in facilitating the selected uniform operating temperature within the chamber.

12. The warming oven according to claim 11, wherein the plurality of heating elements are un-shrouded and are mounted on a reflective ceiling of the housing and are positioned between the reflective ceiling of the housing forming the chamber and a guard formed as a protective grate to facilitate the air flow within the chamber.

13. The warming oven according to claim 1, wherein the air circulator comprises a fan housing for the fan, the fan housing including the exhaust and the intake of the air circulator.

14. The warming oven according to claim 1, wherein the uniform operating temperature facilitated within the chamber is 165 degrees Fahrenheit.

15. The warming oven according to claim 1, wherein the object is a thermoplastic patient immobilization mask for radiation therapy.

16. The warming oven according to claim 1, wherein the temperature sensor is positioned within the chamber in an opposing relationship to the air circulator and at an opposite end of the chamber from the air circulator, and wherein the temperature sensor provides a closed loop operation with the controller to facilitate maintaining the selected uniform operating temperature.

17. The warming oven according to claim 1, wherein the temperature sensor is a thermocouple.

18. The warming oven according to claim 1, wherein the controller includes a proportional-integral-derivative (PID) controller or an analog controller in communication with the plurality of heating elements.

19. A warming device for warming an object for a medical procedure, comprising:

a housing, the housing forming a chamber to receive an object for a medical procedure to be heated, the housing having a heat insulating material adapted to reduce heat transfer from the chamber;

a support member, the support member adapted to be positioned within the chamber and having a support surface adapted to receive and support the object for the medical procedure to be heated;

a plurality of heating elements, the heating elements being arranged within the chamber and in an opposing relationship to the support member, the plurality of heating elements adapted to generate radiant heat in a direction toward the support member and having passages to heat an air flow directed through the passages across the corresponding heating elements; and an air circulator in communication with the chamber, the air circulator including a fan to generate the air flow in the chamber, an exhaust to direct the air flow from the air circulator into the chamber and an intake to receive the air flow returning to the air circulator from the chamber, the air circulator creating a flow path for the generated air flow through the chamber from the exhaust to the intake, the exhaust directing the generated air flow along the flow path in a first direction across the heating elements through the passages of the heating elements to heat the air flow, the plurality of heating elements being adapted to divert a portion of the air flow in the first direction from the flow path in the direction toward the support member to directly engage and mix the diverted portion of the air flow with the air flow in a second direction toward the air circulator to create turbulence in the heated air flow circulating along the flow path in the second direction toward the air circulator to mix the heated air flow and the radiant heat generated by the heating elements with the diverted portion of the air flow in the flow path to provide turbulent heated air to facilitate a uniform operating temperature and uniform heating in the chamber to heat the object for the medical procedure, the generated air flow by the air circulator in the flow path directly engaging and mixing with the diverted portion of the air flow from the plurality of heating elements generating turbulent heated air flow across the object to be heated to provide turbulent heated air to directly impinge upon the object to be heated.

20. The warming device for warming an object for a medical procedure according to claim 19, wherein the object for the medical procedure comprises a thermoplastic object and the uniform operating temperature facilitated within the chamber is 165 degrees Fahrenheit.

21. A warming oven, comprising:
a housing, the housing forming a chamber to receive an object to be heated;
a support member having a support surface adapted to receive and support the object to be heated, the support member being selectively and slidably received within the chamber;
at least one heating element arranged within the chamber in an opposing relationship to the support member, the at least one heating element adapted to generate radiant heat in a direction toward the support member and having at least one passage to heat an air flow directed through the at least one passage across the corresponding at least one heating element;
an air circulator in communication with the chamber, the air circulator including a fan to generate the air flow in the chamber, an exhaust to direct the air flow from the air circulator into the chamber and an intake to receive the air flow returning to the air circulator from the chamber, the air circulator generating an air flow path through the chamber from the exhaust to the intake, the exhaust pushing the generated air flow along the air flow path in a first direction across the at least one heating element to heat the air flow and the intake pulling the air flow in a second direction opposite from the first direction, the at least one heating element being adapted to divert a portion of the air flow in the direction toward the support member to directly engage and mix the diverted portion of the air flow with the air flow in the second direction toward the air circulator to create turbulence in the heated air flow circulating along the air flow path to mix the heated air flow and the radiant heat generated by the at least one heating element with the diverted portion of the air flow in the flow path to provide turbulent heated air to facilitate a uniform operating temperature in the chamber for heating the object, the generated air flow by the air circulator in the flow path directly engaging and mixing with the diverted portion of the air flow from the at least one heating element generating turbulent heated air flow across the object to be heated to provide turbulent heated air to directly impinge upon the object to be heated, and the chamber being a single compartment in which the turbulent heated air flow circulates between the exhaust and the intake of the air circulator;
a temperature sensor to sense a temperature of the air flow in the chamber; and
a controller in communication with the temperature sensor to receive the sensed temperature of the air flow and facilitate maintaining a preselected temperature within the chamber.

22. A warming oven, comprising:
a housing, the housing forming a chamber to receive an object to be heated;
a support member having a support surface adapted to receive and support the object to be heated, the support member being selectively and slidably received within the chamber;
at least one heating element arranged within the chamber in an opposing relationship to the support member, the at least one heating element adapted to generate radiant heat in a direction toward the support member and having at least one passage to heat an air flow directed through the at least one passage across the corresponding at least one heating element;
an air circulator in communication with the chamber, the air circulator including a fan to generate the air flow in the chamber, an exhaust to direct the air flow from the air circulator into the chamber and an intake to receive the air flow returning to the air circulator from the chamber, the air circulator generating an air flow path through the chamber from the exhaust to the intake, the exhaust pushing the generated air flow along the air flow path in a first direction across the at least one heating element to heat the air flow and the intake pulling the air flow in a second direction opposite from the first direction, the at least one heating element being adapted to divert a portion of the air flow in the direction toward the support member to directly engage and mix the diverted portion of the air flow with the air flow in the second direction toward the air circulator to create turbulence in the heated air flow circulating along the air flow path to mix the heated air flow and the radiant heat generated by the at least one heating element with the diverted portion of the air flow in the flow path to provide turbulent heated air to facilitate a uniform operating temperature in the chamber for heating the object, the generated air flow by the air circulator in the flow path directly engaging and mixing with the diverted portion of the air flow from the at least one heating element generating turbulent heated air flow across the object to be heated to provide turbulent heated air to directly impinge upon the object to be heated, and the chamber being without any laminar flow means to hinder turbulence in the turbulent heated air flow;
a temperature sensor to sense a temperature of the air flow in the chamber; and
a controller in communication with the temperature sensor to receive the sensed temperature of the air flow and facilitate maintaining a preselected temperature within the chamber.

* * * * *